(12) United States Patent
Lewis et al.

(10) Patent No.: US 8,842,266 B2
(45) Date of Patent: *Sep. 23, 2014

(54) PHARMACEUTICAL MIXTURE EVALUATION

(75) Inventors: E. Neil Lewis, Brookeville, MD (US); Kenneth S. Haber, Frederick, MD (US)

(73) Assignee: Malvern Instruments Incorporated, Westborough, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/216,038

(22) Filed: Aug. 23, 2011

(65) Prior Publication Data

US 2012/0197541 A1 Aug. 2, 2012

Related U.S. Application Data

(63) Continuation of application No. 11/265,796, filed on Oct. 17, 2005, now Pat. No. 8,004,662.

(60) Provisional application No. 60/619,569, filed on Oct. 15, 2004, provisional application No. 60/627,793, filed on Nov. 12, 2004, provisional application No. 60/643,837, filed on Jan. 14, 2005, provisional application No. 60/645,098, filed on Jan. 20, 2005.

(51) Int. Cl.
*G01N 21/00* (2006.01)
*G01N 21/95* (2006.01)
*A61K 31/00* (2006.01)
*G01N 33/15* (2006.01)

(52) U.S. Cl.
CPC ............ *A61K 31/00* (2013.01); *G01N 21/9508* (2013.01); *G01N 33/15* (2013.01)
USPC .......................................... 356/73

(58) Field of Classification Search
CPC ... G01N 21/9508; G01N 33/15; G01J 3/2823; G01J 2003/2826; B01F 15/00207
USPC .............................................. 356/301, 72–73
See application file for complete search history.

(56) References Cited

U.S. PATENT DOCUMENTS

| | | | |
|---|---|---|---|
| 4,195,930 A | 4/1980 | Delhaye | |
| 4,586,819 A | 5/1986 | Tochigi | |
| 4,859,449 A | 8/1989 | Mattes | |
| 5,271,401 A | 12/1993 | Fishman | |
| 5,288,504 A | 2/1994 | Versic | |
| 5,377,003 A * | 12/1994 | Lewis et al. | ........... 356/300 |
| 5,811,804 A | 9/1998 | Van Blitterswijk | |
| 5,820,558 A | 10/1998 | Chance | |

(Continued)

OTHER PUBLICATIONS

Clarke, Extracting process-related information from pharmaceutical dosage forms using near infrared microscopy:, Vibrational Spectroscopy, 2004, 34, pp. 25-35.

(Continued)

*Primary Examiner* — Kara E Geisel
(74) *Attorney, Agent, or Firm* — Kristofer E. Elbing (57) ABSTRACT

A method of obtaining information about a heterogeneous pharmaceutical mixture is disclosed. This method involves applying an image enhancement agent, such as a stain, to the mixture. An image of the mixture can then be obtained, and information about a distribution of components of the mixture in the image can also be obtained based on spatial information derived from the application of the image enhancement agent.

31 Claims, 5 Drawing Sheets

(56) References Cited

U.S. PATENT DOCUMENTS

| | | | |
|---|---|---|---|
| 6,146,897 | A | 11/2000 | Cohenford et al. |
| 6,275,294 | B1 | 8/2001 | Folestad |
| 6,690,464 | B1 | 2/2004 | Lewis |
| 8,004,662 | B2 * | 8/2011 | Lewis et al. ............ 356/73 |
| 2003/0215791 | A1 | 11/2003 | Garini |
| 2004/0068193 | A1 * | 4/2004 | Barnes et al. .......... 600/476 |
| 2004/0135086 | A1 | 7/2004 | Lewis |
| 2004/0252299 | A9 | 12/2004 | Lemmo |
| 2005/0003550 | A1 | 1/2005 | Kyne |
| 2006/0082762 | A1 | 4/2006 | Leverette |
| 2008/0032412 | A1 | 2/2008 | Lewis |

OTHER PUBLICATIONS

Lyon et al., "Near-Infrared Spectral Imaging for Quality Assurance of Pharmaceutical Products: Analysis of Tablets to Assess Powder Blend Homogeneity", AAPS PharmScitech, 2002, 3(3), Article 17, pp. 1-15.

Scafi et al, "Identification of counterfeit drugs using near-infrared spectroscopy," Analyst, Nov. 19, 2001, 126, pp. 2218-2224.

Buschmann et al, "Spectroscopic Study and Evaluation of Red-Absorbing Flourescent Dyes," Bioconjugate Chem, Nov. 27, 2002, 14, pp. 195-204.

Conte et al, "Modulation of the dissolution profiles from Geomatrix multi-layer matrix tablets containing drugs of different solubility", Biomaterials, 1996, vol. 17, No. 9, pp. 889-896.

Giron et al, "Place of DSC Purity Analysis in Pharmaceutical Development", Journal of Thermal Analysis, 1995, vol. 44, pp. 217-251.

U.S. Appl. No. 11/499,390, including office actions mailed Sep. 23, 2009, Apr. 28, 2010, Nov. 28, 2012, and Nov. 26, 2013: and replies mailed Nov. 23, 2009, Oct. 28, 2010, and Apr. 29, 2013.

U.S. Appl. No. 11/499,390, including office action mailed Jun. 18, 2014, and reply mailed May 27, 2014.

* cited by examiner

PHARMACEUTICAL MIXTURE EVALUATION

This application is a continuation of U.S. application Ser. No. 11/265,796, filed on Oct. 17, 2005 now U.S. Pat. No. 8,004,662. This application also claims the benefit under 35 U.S.C. 119(e) of U.S. provisional application Ser. No. 60/619,569, filed on Oct. 15, 2004, Ser. No. 60/627,793, filed on Nov. 12, 2004, Ser. No. 60/643,837, filed on Jan. 14, 2005, and Ser. No. 60/645,098, filed on Jan. 20, 2005. All of these applications are herein incorporated by reference.

BACKGROUND OF THE INVENTION

It has been recently recognized that the performance of a typical pharmaceutical is not only a function of its chemical composition, but also of its physical makeup. For example, particle sizes and distributions of both the drug and excipients play a role in the final performance of the product. These physical properties can, amongst other things, alter the dissolution profile of a drug, and result in poor or uncontrolled release of the active ingredient into a patient's bloodstream.

Typically, finished pharmaceutical products are a mixture of both the active ingredient and a variety of excipients (lactose, starch, magnesium stearate etc.). During manufacturing these components are physically blended or granulated before being pressed into their final form as tablets. Problems with blending or granulation, such as how well the components have mixed or whether or not there is an agglomeration or preferential association of one or more of the components, can have a significant impact in both the products manufacturability and ability to pass the final quality control tests before product release.

Normally both the active ingredients and the excipients are white powders and visualizing their distribution in either a powder blend, a granulation or a finished product is a challenge. Several analytical approaches are generally taken to assess the heterogeneity of the mixture or finished tablet. These include approaches such as Raman mapping and imaging spectroscopy, as well as infrared and near infrared mapping and imaging. All these approaches produce a map of the distribution of the various chemical components comprising the final product. While these approaches normally result in providing the desired information, they tend to be either slow, expensive, or both. But the information provided is so valuable for understanding an errant manufacturing process that Raman maps are sometimes acquired over a period of several days for a single tablet.

SUMMARY OF THE INVENTION

In one general aspect, the invention features a method of obtaining information about a heterogeneous pharmaceutical mixture. This method includes applying an image enhancement agent to the mixture and then obtaining an image of the mixture. This allows for the derivation of information about a distribution of components of the mixture in the image, based on spatial information derived from the application of the image enhancement agent.

In preferred embodiments, the step of applying can apply a stain as the image enhancement agent. The step of applying can apply a fluorescent stain as the image enhancement agent. The step of applying can apply radiation as the image enhancement agent. The step of applying can apply a stain that is distinguishable in the visible light wavelength range as the image enhancement agent. The step of applying can alter properties of a component in the mixture. The step of applying can alter properties of an inactive component in the mixture. The step of applying can alter properties of an active component in the mixture. The steps of applying, obtaining, and deriving can also be applied to a reference sample. The step of obtaining can obtain an image of the reference sample and the mixture at the same time. The steps of applying, obtaining, and deriving can be applied to a pharmaceutical dosage unit that includes active and inactive ingredients. The stain can have an affinity for one or more of the inactive ingredients. The stain can have an affinity for one or more of the active ingredients. The method can also include exposing at least one inner surface of the pharmaceutical dosage unit, with the step of obtaining an image obtaining an image of the exposed inner surface. Further steps of exposing inner surfaces of the pharmaceutical dosage unit and further steps of obtaining images of the inner surfaces exposed in the further steps of exposing can be used to develop a three-dimensional data set for the dosage unit. The step of exposing can use a cutting implement. The steps of applying, obtaining, and deriving can be applied to a pharmaceutical tablet. The steps of applying, obtaining, and deriving can be applied to a number of different pharmaceutical dosage units obtained from a process at different times. The step of obtaining an image can obtain an image of a plurality of the different pharmaceutical dosage units obtained from the process in a same field of view. The step of deriving can derive a visual presentation of the pharmaceutical dosage unit in which areas affected by the image enhancement agent are presented with a predetermined visual treatment. The steps of applying, obtaining, and deriving can be applied to a number of different samples obtained from a process at different times. The step of obtaining an image can obtain an image of a plurality of the different samples obtained from the process in a same field of view. The steps of applying, obtaining, and deriving can be applied repeatedly to pharmaceutical samples from a commercial pharmaceutical process. The method can further include the step of adjusting the process based on information derived from one or more of the steps of deriving. The steps of applying, obtaining, and deriving can be applied in a sampling regimen sufficient to ensure a predetermined quality objective for the pharmaceutical mixture. The steps of applying, obtaining, and deriving can be performed without stopping the process. The steps of applying, obtaining, and deriving can be performed during an interruption of the process. The steps of applying, obtaining, and deriving can be applied to pharmaceutical samples from an experimental pharmaceutical process. The method can further include the step of adjusting a formulation for the pharmaceutical mixture. The step of deriving can derive statistical information about the distribution of components of the mixture. The step of deriving can derive statistical information about particle size for components of the mixture. The step of deriving can derive statistical information about particle distribution for components of the mixture. The method can further include the step of comparing results from the steps of applying, obtaining, and deriving for a first sample of the pharmaceutical mixture with results from the steps of applying, obtaining, and deriving for at least a second sample of the pharmaceutical mixture. The step of comparing can include deriving statistical information about a number of samples of the pharmaceutical mixture. The method can further include the step of comparing results from the steps of applying, obtaining, and deriving with a predetermined standard. The method can further include the step of providing an indication of origin of the mixture based on the information derived in the step of deriving. The step of providing an indication of origin can be operative to provide a genuine/counterfeit indication. The method can further include the step of providing a cleaning validation indication based on the information derived in the step of deriving. The method can further include the step of determining a root cause of a manufacturing process defect for the mixture based on the information derived in the step of deriving. The step of applying can apply the stain using vapor deposition.

In another general aspect, the invention features an apparatus for obtaining information about a heterogeneous pharmaceutical mixture. This apparatus includes an image acquisition system having a field of view operative to acquire images of samples of the pharmaceutical mixture, and an image enhancement detection module optimized to detect portions of the mixture having been exposed to a predetermined image enhancement agent. An information derivation module is operative to derive information about a distribution of components of the mixture in the image, based on spatial information derived from the image enhancement detection module.

In a further general aspect, the invention features an apparatus for obtaining information about a heterogeneous pharmaceutical mixture that includes an image enhancement treatment applicator operative to apply an image enhancement treatment to a least one of the samples, and an image acquisition system operative to acquire images of the samples.

In preferred embodiments, the apparatus can further include a staining area, an actuator for transporting samples of the pharmaceutical mixture from a first location to the staining area, and wherein the image enhancement treatment applicator is operative to apply the image enhancement treatment to a least one of the samples in the staining area. The actuator can be positioned to automatically extract the samples from a commercial pharmaceutical process at predetermined intervals.

In another general aspect, the invention features a chemical imaging system for pharmaceutical analysis. It includes a spectrometric imaging detector having a first sensitivity range between a first wavelength and a second wavelength longer than the first wavelength, wherein the spectrometric imaging detector is operative to acquire an image of a pharmaceutical mixture in a sample area. It also includes a spectrometric point detector having a second sensitivity range between a third wavelength and a fourth wavelength longer than the third wavelength, wherein the first and second wavelengths ranges are different, wherein the spectrometric point detector is operative to acquire a reading of the pharmaceutical mixture in the sample area. A synthesis module is responsive to the imaging detector and to the point detector and is operative to operate on output from the imaging detector and output from the point detector to obtain a quality metric for the pharmaceutical mixture.

In preferred embodiments, the quality metric can include a chemical image of the pharmaceutical mixture. The pharmaceutical mixture can be in the form of a pharmaceutical tablet. The apparatus can further include threshold detection logic operative to determine whether the quality metric meets a predetermined quality standard. The apparatus can further include threshold detection logic operative to determine whether the quality metric meets a predetermined origin standard. The apparatus can further include threshold detection logic operative to determine whether the quality metric meets a predetermined authenticity standard. The apparatus can further include statistical analysis logic operative to derive statistical information about the spatial distribution of components of the mixture. The statistical analysis logic can be operative to derive information about particle size for components of the mixture. The statistical analysis logic can be operative to derive information about particle distribution for components of the mixture. The apparatus can further include a radiation source positioned to illuminate the sample. The radiation source can be an ultraviolet light emitting diode. The radiation source can be a visible light emitting diode. The apparatus can further include a plurality of radiation sources positioned to illuminate the sample. The spectrometric point detector can be a Raman point detector. The spectrometric point detector can be an infrared point detector. The spectrometric point detector can be a near infrared point detector. The apparatus can further include at least one spectrally selective element between a radiation source and the imaging detector. The chemical imaging system can be operative to acquire an image of a reference with the image of the pharmaceutical mixture.

In a further general aspect, the invention features a chemical imaging system for pharmaceutical analysis that includes a first spectrometric imaging detector having a first sensitivity range between a first wavelength and a second wavelength longer than the first wavelength, and being operative to detect values of a first property of a plurality of image elements for components of a sample of a pharmaceutical mixture in a two-dimensional image space. Also included is a library populated with a priori image element mapping knowledge entries. A mapping module is operative to access the library and to operate on output from the imaging detector to enable the representation of values of a second property of the plurality of image elements for the components of the sample of the pharmaceutical mixture based on the values of the first property and at least one of the entries in the library.

In preferred embodiments, the a priori knowledge can be derived from the same type of sample by a second imaging detector having a second sensitivity range between a third wavelength and a fourth wavelength longer than the third wavelength, with the first and second wavelengths ranges being different. The a priori knowledge can be derived from knowledge about a scope of possible components of the sample.

In another general aspect, the invention features a chemical imaging system for pharmaceutical analysis that includes a radiation source operative to cause at least one component of a continuous sample of a pharmaceutical mixture to fluoresce in a sample area, a spectrometric fluorescence imaging detector having a first sensitivity range between a first wavelength and a second wavelength longer than the first wavelength, wherein the spectrometric fluorescence imaging detector is operative to acquire an image of the pharmaceutical mixture in a sample area while it fluoresces, and a processing module responsive to the spectrometric fluorescence imaging detector and being operative to obtain a chemical image that includes information about the spatial distribution of components of the pharmaceutical mixture within the continuous sample.

In a further general aspect, the invention features a chemical imaging method for pharmaceutical analysis that includes detecting values of a first property of a plurality of image elements for components of a sample of a pharmaceutical mixture in a two-dimensional image space in a first wavelength range between a first wavelength and a second wavelength longer than the first wavelength. It also includes obtaining at least one a priori image element mapping knowledge entry from a library, and accessing the library and operating on output from the imaging detector to enable the representation of values of a second property of the plurality of image elements for the components of the sample of the pharmaceutical mixture based on the values of the first property and the at least one entry in the library.

In another general aspect, the invention features a chemical imaging system for pharmaceutical analysis that includes an imaging spectrometer and a processing vessel proximate the spectrometer and having at least one wall having inside and outside surfaces. At least a portion of the wall within a field of view of the imaging spectrometer is a window that includes a non-stick material on its inside surface.

In preferred embodiments, the window can be constructed with a fluoropolymer as the non-stick material. The window can be constructed with polytetraflouoroethylene as the non-stick material. The window can be constructed with a structural material in addition to the non-stick material. The structural material can be sapphire and the non-stick material can be a fluoropolymer. The imaging spectrometer can be a near-infrared imaging spectrometer. The imaging spectrometer can be an ultraviolet imaging spectrometer. The imaging spectrometer can be a visible-wavelength imaging spectrometer.

In a further general aspect, the invention features a chemical imaging method for pharmaceutical analysis that includes providing a pharmaceutical mixture including a plurality of ingredients, receiving radiation reflected from the ingredients in the pharmaceutical mixture at a number of frequencies through a material that does not adhere to the ingredients in the pharmaceutical mixture, and obtaining a chemical image of the pharmaceutical mixture from the received radiation.

In preferred embodiments, the method can further include the step of analyzing the chemical image to evaluate mixing of the pharmaceutical mixture. The step of receiving can receive radiation reflected from the pharmaceutical mixture at a number of frequencies through a material that does not adhere to ingredients in the pharmaceutical mixture when heated to above 60 degrees Celsius.

Systems according to the invention are advantageous in that they can allow information about the physical makeup of a pharmaceutical mixture to be obtained quickly and inexpensively. These capabilities can speed up the development of pharmaceuticals and the process equipment used to manufacture them. They can also reduce the cost of the development and ramp-up of a suitable manufacturing process.

Systems according to the invention can also be very useful as quality assessment and quality control tools. Because of their high speed and low cost, these systems can process large numbers of tablets or other aliquots of a pharmaceutical mixture to monitor a large-scale or ongoing pharmaceutical manufacturing process. This can allow pharmaceutical manufacturers to set and achieve quality standards for the physical makeup of their products.

And because systems according to the invention can operate quickly, they can be deployed in such a way as to monitor a process in real time or near real time. This can allow manufacturers to quickly detect and correct a situation in which a process has developed a defect, reducing the amount of wasted product and catch-up time required to replace that product. Because of the abundance of information that is potentially available, systems according to the invention may even be able to monitor trends in a process and correct them before they result in an error condition in which product must be discarded.

DETAILED DESCRIPTION OF AN ILLUSTRATIVE EMBODIMENT

Figure 1:
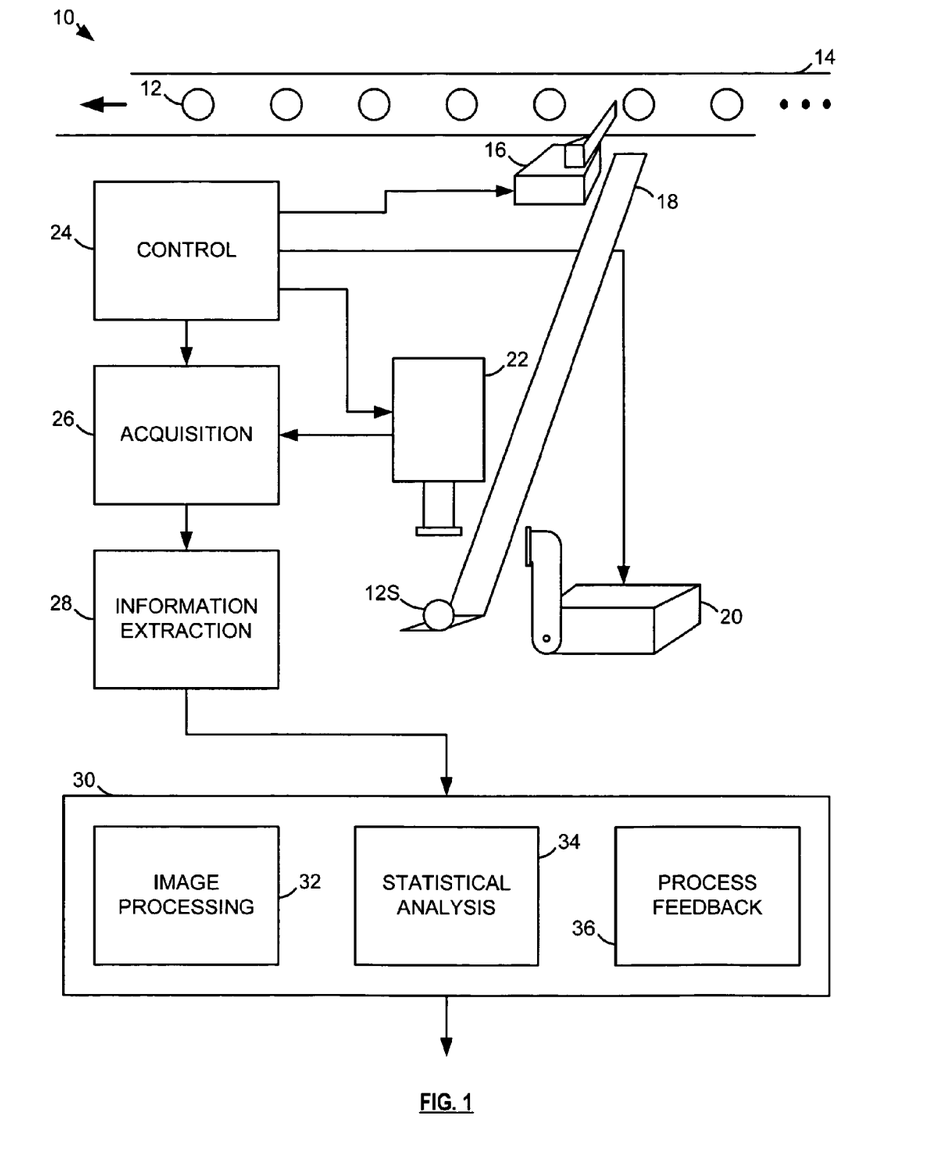
FIG. 1 is a block diagram of an illustrative embodiment of a pharmaceutical mixture quality control system according to the invention.
Figure 2:
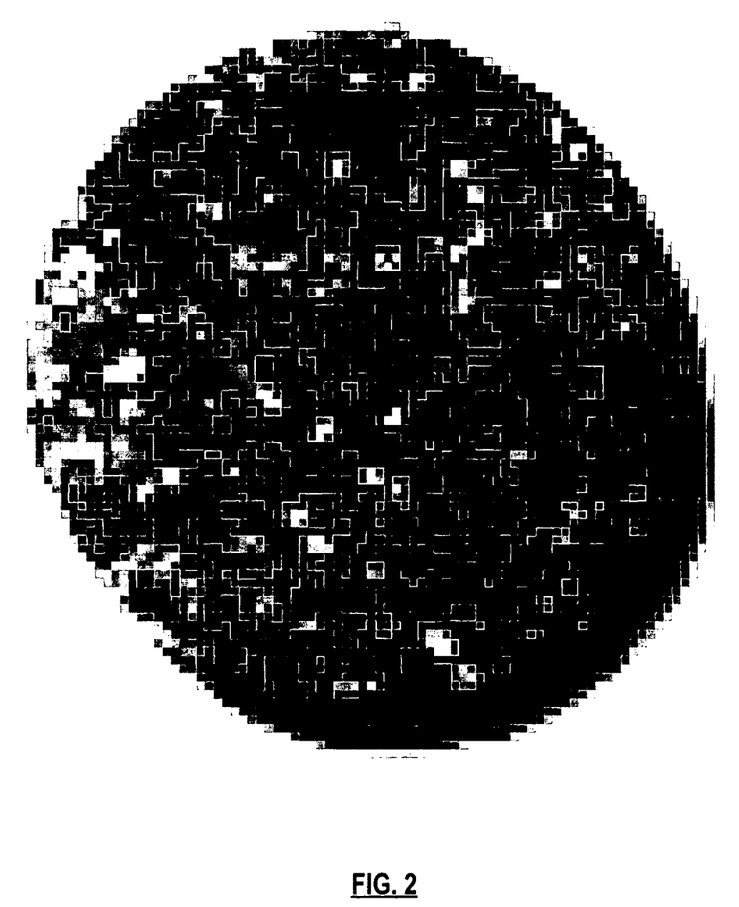
FIG. 2 is an image of an analgesic tablet that was stained with iodine and acquired in accordance with the invention.

Referring to FIG. 1, an illustrative embodiment of the invention includes an information acquisition system 10 that can be placed proximate a processing device. In this illustrative embodiment, the acquisition operates in concert with a conveyor 14 that transports pharmaceutical dosage units 12, such as tablets. Other types of processing devices could also be accommodated, however, such as hoppers, blenders, or granulators. And other types of pharmaceutical mixtures or dosage units can be provided for, such as bulk powders, capsules, suspensions, or even mixtures of immiscible fluids.

The acquisition system can include an actuator that transports a sample (e.g., 12S) from the processing facility to a sample area. In this illustrative embodiment, the actuator includes a controllable diverter 16 that selectively diverts tablets onto a ramp 18. But one of ordinary skill would of course recognize that other types of actuators can also be provided to obtain samples from a conveyor, such as different types of mechanical actuators, pneumatic nozzles, vacuum fixtures, or electrostatic collectors. The actuator may also be implemented differently depending on the nature of the sampling process required. To extract material from a blender, for example, the actuator can employ a small sampling shovel mounted on a moving carriage.

The acquisition system 10 also includes an imaging enhancement agent applicator 20. In this illustrative embodiment the applicator can include a stain pad similar to an office stamp pad, and an application mechanism to press the pad against the dosage unit. The stain could also be placed in a sealed package as a disposable (one dose) strip and be applied by pressing the strip to the tablet and then removing. Other types of applicators can also apply a stain to the dosage unit, such as other types of stamping mechanisms, aerosol nozzles, or dipping mechanisms. Vapor deposition is another suitable way of applying a stain. Iodine, for example, can be sublimated and delivered to a chamber in which it condenses on a surface of the dosage unit.

The tablet may be stained with a colorless stain that reacts with one of the components within the tablet to produce a color change. The stain may also be colored, but this would still result in a color change on contact with the tablet. The stain is preferably a visible stain, but it can also be a stain that provides information outside of the visible wavelength, such as an ultraviolet or infrared fluorescence stain. For example, many pharmaceutical active ingredients are aromatic compounds for which a particular visible or fluorescent stain could be identified or explicitly manufactured, while most of the commonly used excipients (e.g., compression/encapsulation aids, disintegrants) are not aromatics. Further, other ingredients, such as starch, could be readily stained using compounds such as iodine. Using an array of stains and fluorophores one, some or all of the components of the tablet could be stained, and then digitally imaged with either a macroscopic or microscopic visible imaging system. The imaging enhancement agent may also take another form, such as a gas, radiation or even heat.

The acquisition system 10 also includes an image sensing system 22. This system can include a camera that is sensitive to visible wavelengths and is equipped with suitable lenses. The imaging system can produce simple RGB type pictures or may be fitted with one or more optical filters to highlight color absorption or fluorescence emission characteristic of a particular stain or tag and therefore of a particular component of the pharmaceutical product. This image can be obtained while the sample is in the staining area, or in another imaging area. The camera may be held at a fixed position, or moved in and out of position.

Tablets may be stained one at a time or in arrays. For example, a plate containing 96 or more tablets may be stained simultaneously before being placed in the field of view of the camera. The entire 96 tablet sample may comprise individual tablets removed from a production line at known time intervals to provide a statistical sampling of the evolution of a process or manufacturing run. Suitable robotic handling machinery to load multi-sample plates is available from, for example, Caliper Life Sciences, of Hopkinton, Mass. Of course, any type of information derived from compound images can also be derived from a series of individual images.

One or more reference samples can also be provided in the field of view of the camera to act as a standard for measurements made on the images. These reference samples could be known-good aliquots of the mixture to be tested, or they may include other reference materials, such as one or more single components of the mixture. A supply of reference samples may be provided such that they are stained along with, or between, some or all of the samples under test. One or more pre-stained reference samples could also be positioned at a fixed position near the sample under test and used repeatedly. The use of a reference sample and other relevant topics are discussed in U.S. Pat. No. 6,690,464, entitled "High-Volume On-Line Spectroscopic Composition Testing of Manufactured Pharmaceutical Dosage Units," issued Feb. 10, 2004, and which is herein incorporated by reference.

As the imaging sensing system 22 acquires image data, it passes them on to an acquisition system 26, which assembles the data into an image. An information extraction module then extracts information about the spatial distribution of stain in the image. This extraction of information can be a relatively simple operation, such as mapping of data into a color image, or it can involve some degree of spectral processing or image processing to enhance the spatial information.

If needed, further processing logic 30 can perform additional operations on the data. The user can use an image processing module 32, for example, to perform further image processing operations on the image. The user can also use a statistical analysis module 34 to derive statistical information about a spatial distribution within a particular sample, or to derive information about trends within a series of samples.

The statistical analysis module 34 can provide its output in a variety of forms, including raw numbers, graphs, or images that can be presented on an output device, such as a display or printer. It can derive and analyze the relative frequency distribution of concentration for one or more substances. It may also calculate a mean, skew, and/or kurtosis for the distribution. The mean provides an indication of the overall concentration or amount of an item or substance analyzed. In the case of a pharmaceutical dosage unit, for example, the mean provides a measure of its dosage. The standard deviation can provide for a measure of the range of variation of certain properties, such as film thickness. Skew and kurtosis both provide an indication of non-uniformity of mixing or non-normal statistical distribution in a sample. These quantities can be evaluated as absolute numbers or in comparison with earlier results. The statistical analysis logic can also perform its analysis on more than one chemical component or property, and it can detect and analyze overlapping distributions, such as by curve fitting. The application of statistical techniques to particular images and other relevant topics are disclosed in published PCT Application No. WO03060443, which is entitled "Spectrometric Process Monitoring" and corresponds to U.S. Ser. Nos. 60/343,449, 60/343,691, 60/394,053, and 60/394,053. All five of these documents are herein incorporated by reference.

It is also possible to make more than one measurement for each sample by exposing inner surfaces of the sample and staining them. Suitable techniques for this type of operation and other relevant topics are described in U.S. application Ser. No. 10/684,965, which is entitled "Volumetric Spectral Imaging" and was published under Publication No. 20040135086. This application is herein incorporated by reference.

The system can also include process feedback logic 36, which allows the spatial distribution information to be fed back into the process. This feedback logic can be configured to provide recommendations for changes to the process or it can automatically issue signals to a process device. For example, the feedback logic could provide limits on statistical particle distribution parameters above which a signal would be sent to a blender to adjust one of its operating parameters, such as blend speed or blend time. The feedback logic may also alert an operator or indicate when an entire batch should be discarded.

The system can be used outside of quality control/quality assurance and process monitoring context. It may be used as a development tool in drug development and formulation. It may also be used to establish the root cause of manufacturing problems as they may arise. It may be used for cleaning validation to ensure that one process does not affect a subsequent one that is run using the same equipment. And it may even be used outside of the manufacturer's facilities altogether in the in the identification of recalled, counterfeit, or gray market products.

A single tablet could be multiply stained or multiple tablets can be used, each with a single chemical marker. One stain could be specific to different polarities corresponding to chemical components of the tablet, for example, and another could be specific to their different hydrophobicities. The multiple images collected from such a series of optical filters or multiple stains may be further processed using standard image processing methods or other mathematical algorithms such as univariate or multivariate statistical methods. While the tablet being stained would likely be contaminated and lost to the manufacturing process, the speed of the technique might facilitate its use near a pharmaceutical manufacturing line where it might sample 1 in 100 or 1 in 1000 tablets actually manufactured. These stained tablets would be discarded, but would provide a good statistical representation of a finished tablet, a granulation or a powder blend. Additionally, using digital image processing techniques, discrete or continuous sample statistics may be collected for a particular manufacturing process which could potentially identify emerging problems before a process goes out of control. Using particle statistics to measure the area of the tablet stained and the intensity of the light absorption or emission, an estimation of the composition may be obtained in addition to the physical information returned on the particle size and distribution statistics provided by the image.

Each of the operations described above can be performed manually, or they may be fully or partially automated. It may make sense in some circumstances, for example, to use an automated sampling mechanism to obtain an appropriate set of samples, but to then manually stain them, position them in the field of view of the camera, and evaluate the resulting images. Or it may be appropriate in some instances to sample, stain, and obtain images manually, but then to rely on an automated software assessment of the results.

In one embodiment, the system is based on the so-called IBM-PC architecture, with the image acquisition interface 26 and image processing module 32 being implemented in hardware as plug-in boards occupying expansion slots on the system bus, and remaining functionality being implemented in software. Of course, other structures can be used to implement systems according to the invention, including various combinations of dedicated hardware and special-purpose software running on general-purpose hardware. In addition, the various elements and steps described can be reorganized, divided, and combined in different ways without departing from the scope and spirit of the invention. It should also be noted that not all of the items presented in the discussion of the illustrative embodiment will be required for all implementations of the invention.

There is considerable interest in measuring not only the potency and purity of a pharmaceutical product but also interest in determining the chemical 'structure' of the product. Most solid-dosage pharmaceuticals are spatially heterogeneous materials comprising mixture of powders. These powders are typically pressed into a finished product which can be a tablet. Because of the disparate nature of the various components there can occur non-uniform distribution of components in the final product. These can be the result of aggregation of one or more components and or the preferential association of components. These inhomogeneities can be the result of physical forces imparted on the product during the manufacturing process or the result of other factors such as electrostatic charge, hydrophobicity, particle size and de-mixing etc. In either case while the exact composition of the entire tablet may be well characterized the physical distribution of the components may not. In other words pharmaceutical companies may know what and how much of each component is in the tablet but do not always know where it is or how it is distributed.

The concept of staining biological tissue to reveal structural detail at the cellular level is a well established technology. Stains are also used to study dissolved pharmaceutical compounds under either visible or ultraviolet light. In the latter case the method proceeds by dissolving a tablet and extracting the active ingredient with chromatographic techniques such as thin-layer chromatography (TLC). Detection techniques that may include staining are then used to visualize the presence of the active ingredient as spots on a TLC plate. In the latter case no structural information about the tablet is available and the excipients (non-active ingredients) are normally not measured and considered unimportant to the quality of the product. The entire process is designed to only measure the presence of the drug and to give an indication of the amount and/or purity. These are principal parameters determined by the USFDA for determining the quality of the finished product and its fitness for release to the public.

Presented here is the concept of physically staining and imaging a finished and intact pharmaceutical product with a variety of materials that are selective for the different components that comprise a typical drug product. These stains can determine component blending and particle size and particle size distribution of both excipients and active pharmaceutical ingredient(s). These images can be used as an additional and critical measurement of product quality. This spatial information may be a critical component in how a particular product behaves when ingested. For example, these physical factors may affect the dissolution characteristics and cause the product to release the drug into the blood stream either too quickly or too slowly. In another situation the performance of the product may not be impacted, but the manufacturability might be. Lack of optimum blending characteristics may result in tablets that stick in the tablet press or tablets that crack chip or break easily resulting in loss of production time or products that cannot be sold for aesthetic reasons. In another situation the spatial distribution of components in a tablet may be a design element such as in a time-release or sustained release product. In another situation a product may be a drug product containing two or more ingredients designed to be delivered to the patient in succession and not simultaneously. In these situations the physical composition of the tablet is a critical design parameter and one for which there is little current technology to address, especially in a manufacturing setting. Another use of the technology may be in the visualization and discovery of counterfeit pharmaceutical products. These products are likely to be produced using different manufacturing processes and while the active ingredient may be correct the different process may result in a different distribution and size distribution of the components. This pattern would be the 'fingerprint' of the original and counterfeit products.

The stains may be observed in the ultraviolet, visible or near-infrared part of the optical spectrum. The stains may be simple absorption stains or fluorescent or bio-luminescent stains. The preferential component staining can be achieved with stains that either preferentially bind with one or more components or that react with one or more components to achieve a color change or preferential color localization. For example, Sudan Red (a stain for wax) or others stains such as Furaptra(AM) or Indo-Mag(AM) may be used to preferentially visualize the distribution of Magnesium Stearate. Stains that are specific for Sodium, Magnesium of Calcium may be used to visualize the distribution of excipients such as calcium phosphate, sodium phosphase or magnesium stearate. Iodine may be used to visualize starch or the active ingredient. A myriad of highly selective stains are available and can be used to 'stain' for different functional groups. They may be used singly or in combination to highlight the distribution of one or more components. As another example a pH indicator may be used to preferentially visualize materials in the matrix with slightly or grossly varying pH values. In another mode the tablet may just be subjected to a chemical etching technique where it is subjected to selective dissolution by suitable solvents. In this mode some of the crystals for one or more components in the tablet would be dissolved and the tablet effectively etched. The etching process would serve to reveal the location of these species in the subsequent imaging step.

Finished tablets may be visualized using this technique but it is also useful to apply the technique to other parts of the manufacturing process. Tablets may be stained and examined before or after coating. Pharmaceutical granules from a granulation process may be imaged before being pressed into the final tablet form. A powder blend may be stained and examined for homogeneity of mixing. The technique could be used during manufacturing or during formulation development to determine the distribution properties of the individual components. The technique could also be used in a troubleshooting or root-cause analysis mode and these imaging instruments may be used either in a laboratory or in a manufacturing environment. They may be used in an in-line, at-line or near-line capacity to support quality assurance or quality control measurements. The technology is rapid and will also have utility in the new USFDA PAT initiative. The technology may also be employed in a 'field' mode and used to support efforts to determine counterfeit pharmaceutical products as they pass through international borders, ports or airports.

The visualization process may take the form of simply looking at the stained product with the naked eye or through a microscope to visualize the more minute structures and particles. Preferably the data is recorded digitally with a camera, CCD or focal-plane array detector. These data can be stored and subjected to further more quantitative image analysis. Simple color (RGB) type cameras may be used but more sophisticated spectral imaging approaches may also be used. These methods would take images of the samples at multiple wavelengths to provide enhanced discrimination of the various components which may be preferentially stained by one or more of the 'stains'. In addition, a wavelength filter in conjunction with a high dynamic range camera such as a CCD would provide much more accurate color depth information than a simple RGB camera or viewing with the naked eye. This information would provide a much more accurate assessment and discrimination of the different chemical species. The wavelength selection filters may be simple color filters used singly or in combination but may also be more sophisticated filter wheel arrangements or even tunable filters such as AOTFs or LCTFs. The filters may be narrow bandpass optical filters, broad bandpass optical filters or short and/or longpass optical filters. The filters may be used to filter the incident light and also to filter the reflected or emitted light. The samples may be illuminated with narrow band light (lasers etc.) or broad band light. The samples may be illuminated with visible light, ultraviolet light or infrared light. For example, the samples may be illuminated with broad band ultraviolet light and measured by capturing emitted visible light. The physical phenomena by which spatial contrast is derived from the various components may be by absorption or fluorescence emission.

The method by which the stains may be applied to either a finished product or intermediate may be varied. The device may be a chamber into which one or more tablets are placed for the application of the stain by an aerosol system or other means of producing a means of uniformly applying the stain in a non-contact mode. The device may include a pad or adhesive strip containing a stain or other such contact type applicator. The stain applicator may also be of a type similar to the inkjet deposition technology currently used in printers or some other autopipetting technology. In either case the applicator may be refillable or disposable providing a continuing revenue stream. The stain applicator may be able to apply a stain of only a single type of may be configured with one or more applicators to be able to apply different stains and/or multiple stains. For example, a stain applicator might have one or more inkjet type cartridge locations which may be swapped out for different cartridges or replacement cartridges. The device may also contain one or more solvent applicators for the removal of excess stain from the tablet or for cleaning the various applicators. The device may be capable of staining single tablets, granules or tablet blends but may be also capable of staining multiple tablets, granules or multiple powder samples simultaneously. The system may operate continuously, semi-continuously or in a 'static' laboratory type mode. For example, tablets may be able to move continuously through the system in a manner analogous to a car wash for a fully automated manufacturing application but may also be hand-loaded for near-line or laboratory type applications. The staining system may be manually operated on single samples while the imaging system may be automatic and allow multiple samples to be loaded. The staining system may be automatic while the imaging portion could be done manually or both be automatic or both be manual. Indeed the entire system may be integrated such that staining and imaging are done with a single piece of apparatus. Clearly the staining device might be sold separately or in conjunction with the imaging system and the staining system might be used in conjunction with a standard microscope of other digital imaging system. The device may also come equipped with a timer and other measuring systems for ensuring the correct application of the stain but may also be able to time a staining process to ensure that a particular reaction has completed. It may also include a heater, or light source which may be used in conjunction with the staining process to finish the tablet preparation before being imaged. For example, after the application of a stain a solvent may need to be evaporated before the imaging process should begin. These issues can be automatically controlled by this device. The device may also be connected to an air and solvent handling system for the proper collection and disposal of any toxic materials associated with the staining process. It is also possible that the stain applicator may take the form of a simple 'marker pen' type format for field use.

In both laboratory and manufacturing or quality control applications the technology may be used in conjunction with other well-established analytical methods such as HPLC, near infrared spectroscopy, Raman spectroscopy, mid-infrared spectroscopy. These other techniques would provide the additional potency and purity data necessary to fully characterize the product. The technique may also be used in conjunction with existing chemical imaging systems such as near-infrared, mid-infrared or Raman imaging systems. These systems may also be imaging systems of the mapping variety. These auxiliary spectroscopic measurements may measure the samples in either a macro or micro mode. In a macro mode the chemical composition of the whole product is measured in conjunction with the imaging data. In the microscopic mode individual locations within the product may be determined from the stained image for further analysis by a NIR, Raman or mid-infrared spectrometer. For example, a particle that stains a particular color or has a particular visible spectral distribution as determined by a tunable filter configuration can be measured by a standard analytical spectrometer to absolutely identify it. The stained image may then be interpreted on the basis of this information. In other words all crystals stained the same color or with the same visible spectral distribution may be interpreted as being of the same chemical composition as the crystal measured by the spectrometer. Other stained crystals may be similarly assessed. Abundance (quantitative) estimates of the total composition may be determined from measuring the area of coverage of a particular stained component. A tablet may also be crushed and spread onto a surface before staining and imaging. While any spatial information would be lost, in some cases this may give a better estimation of the total composition of the finished product.

A staining system may comprise just the imaging device, just the staining device or a combination of the two. It may further include one of the aforementioned spectrometers. In another configuration this type of staining and imaging system may be tied directly to existing HPLC or spectroscopic equipment and/or microscopes from other manufacturers.

In another configuration a system may be assembled expressly for attaching to a pharmaceutical manufacturing apparatus such as a blender, granulator, tablet press or blister packaging machine. For example, in the blending configuration an automated system for retrieving small (unit dose) quantities of the mixture from the blender may be interfaced with a staining and imaging unit. In operation the sample is retrieved and quickly pressed into a tablet or wafer format. The stain is applied and the wafer imaged. The data can be analyzed to determine the distribution of one or more components before the wafer is discarded. The system can stain multiple wafers at discreet time intervals as the blending process progresses. In this manner the blending process may be terminated when optimum mixing statistics are determined. In a manner described previously the multiple stains can be applied to multiple or single wafers to determine the distribution of multiple components of interest. Also this type of imaging system may be used singly or in combination with another on-line measurement technology such as near-infrared spectroscopy, Raman spectroscopy or mid-infrared spectroscopy. Similar approaches may be used for monitoring a granulation process and the component distribution and stoichiometry of a granulation process. In another configuration a tablet may be retrieved from a tablet press at different time intervals to monitor the distribution of one of more components and determine the uniformity of a coating process. One tablet in 100 or one tablet in 1000 may be retrieved. These tablets would of course, once stained, be lost to the manufacturing process.

Image processing methods for analyzing the image contrast may be both qualitative and quantitative. Individual images may be analyzed using standard techniques to enhance contrast and segment the images. The images may be analyzed using particle statistics to measure particle size and distribution of one or more components. The statistics may be visualized as histograms or other graphical means to represent mixing or particle distributions. The statistics can return information on mean values as well as deviations from the mean which might indicate a manufacturing or quality control problem. Multiple images derived from multi-wavelength filter based approaches may be analyzed using multivariate statistics in a manner similar to conventional chemical imaging data. One or up to three of these images for single or multiple stains may be combined in a simple RGB image, or multiple stains visualized in a binary stack motif where single colors in an image represent a single chemical species. The distribution of multiple chemical species may be determined using either multiple or single stains and the data processed to segment each component and highlight its distribution.

Imaging of pharmaceutical products is of interest because it is now realized that in addition to the chemical composition, the spatial relationship and size of the chemical domains comprising a complex formulation can also play a role in the ultimate performance and/or quality of a pharmaceutical product.

This application describes a system that combines the ability to obtain either simultaneously or in quick succession both chemical and spatial information from a single pharmaceutical product. Existing systems to accomplish this use sophisticated chemical imaging techniques such as infrared, Raman or near-infrared spectral imaging or mapping instruments. These are typically expensive, complex and in some cases slow. This concept stems from recognizing that the issue of spatial information and chemical information within a pharmaceutical formulation, tablet or mixture can be separated by using two different non-invasive analytical protocols. Proposed in this application is a single instrument that combines visible or fluorescence imaging with a single point infrared, near-infrared or Raman instrument to provide spatial information in the former and chemical information in the latter. For example, a tablet may be placed in an instrument and simultaneously probed by an optical beam to collect a single mean infrared, Raman or near-infrared spectrum while a second optical beam in a different wavelength range can be used to image the sample using fluorescence excitation. These two data streams may be combined to derive a single metric that describes both the spatial and chemical content of the tablet. In another instance the molecular spectroscopy probe may immediately proceed the imaging of the tablet since the imaging may require the addition of a contrast enhancement agent that would affect the prior spectral measurement, as described in Application Ser. No. 60/619,569, filed Oct. 15, 2004, and Application Ser. No. 60/627,793, filed Nov. 12, 2004 and both entitled "Pharmaceutical Mixture Evaluation," which are herein incorporated by reference. In another instance the fluorescence or other type of imaging may precede the spectral/chemical measurement and be used to identify regions of interest to subsequently probe with a microbeam from the molecular spectroscopy instrument (Raman, IR, NIR). The imaging and spectroscopic measurement can also be performed simultaneously.

The proposed instrument design can use an imaging technique (fluorescence, or visible absorption) that has less chemical specificity that those methods currently used (Raman, IR or NIR). However, its performance can be enhanced by using multispectral or hyperspectral approaches. For example, a tablet may be subjected to incident UV or visible radiation at a series of wavelengths and imaged at each separate excitation wavelength or may be excited at a single visible or UV wavelength and imaged at a series of emission wavelengths using one or more optical bandpass filters, or a tunable optical filter such as an AOTF or LCTF. Changes to the excitation and emission selectivity can of course also take place simultaneously, such as in the case of a synchronous or 2-dimensional fluorescence measurement. An interferometer may also be used as a means of producing a modulated excitation radiation or as a means of measuring emission radiation. In either case one of more images of a sample may be produced which can be subjected to further qualitative and quantitative analysis to determine particle sizes and particle size distributions which may be used to infer the quality of performance of a pharmaceutical product or manufacturing process. In the case of hyperspectral or multispectral fluorescence or visible absorption measurements the derived digital data can be compared and contrasted to fluorescence or visible absorption spectra of pharmaceutical excipients or active pharmaceutical ingredients previously measured and stored in a spectral library. These comparisons or matches may be done using a variety of univariate or multivariate mathematical approaches. In another example a near-infrared, infrared or Raman chemical imaging data set of a particular tablet, granule or pharmaceutical blend may be collected and the same tablet subsequently imaged using visible staining or fluorescence imaging. Both data sets may be combined to produce a correspondence table, which can be a 'one-to-one' lookup table such that the chemical identity of the particle or spatial location is derived from the infrared, Raman or near-infrared data and stored with the corresponding visible/fluorescence spectrum. For subsequent tablets, granules or powder blends of the same product measuring the fluorescence or visible imaging data and use of the pre-determined 'look-up' table will enable the location of the various chemical components to be derived using this simpler, quicker and less expensive approach.

For the fluorescence measurements one or more UV and/or visible light emitting diodes (LEDs) or laser diodes may be used to perform the imaging measurements at different excitation wavelengths, as described in PCT application WO 01/61293, published Aug. 23, 2001, entitled "Multi-Source Spectrometry" and herein incorporated by reference. This imaging technique alone or in combination with another single-point spectroscopy such as infrared, Raman or near infrared in addition to providing quality assurance and quality control tools for pharmaceutical manufacturing can also provide a rapid and simple method for determining counterfeit pharmaceuticals.

Figure 3:
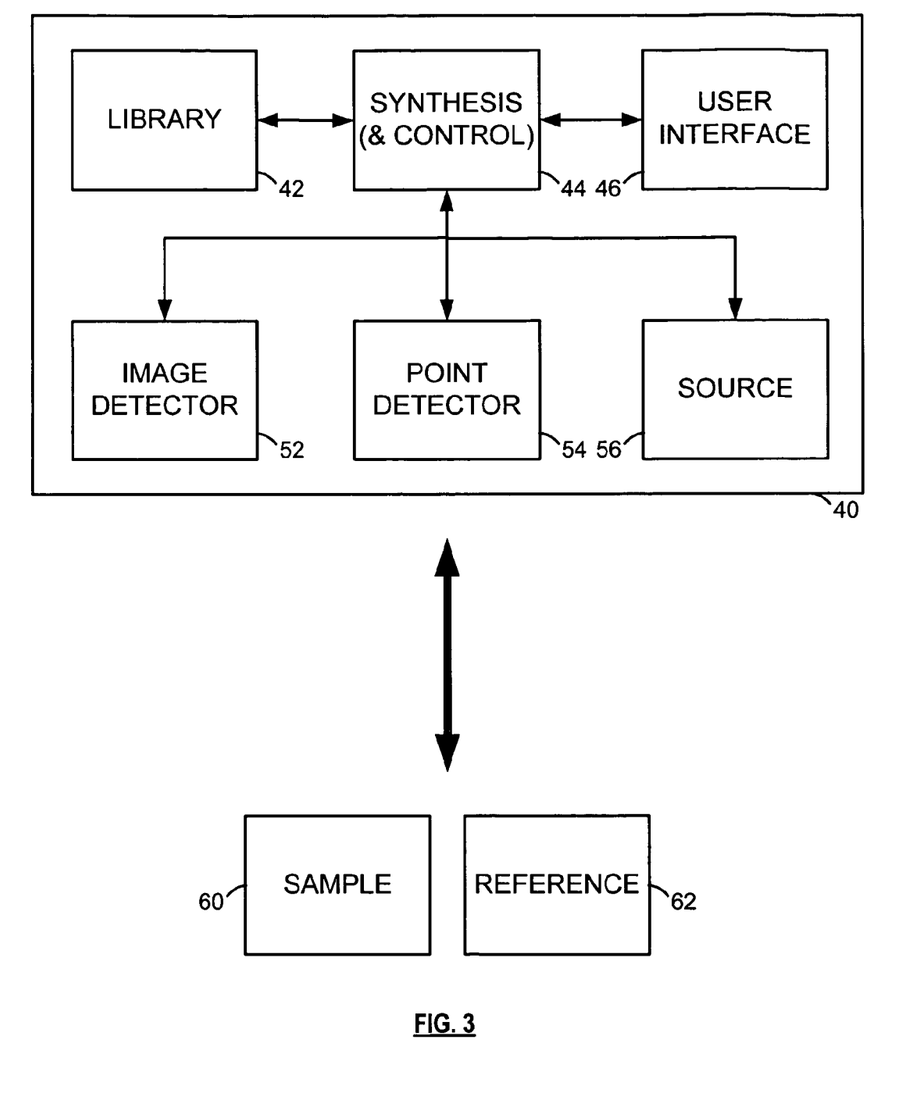
FIG. 3 is a block diagram of an illustrative embodiment of a chemical imaging system employing dual disparate detectors.

Referring to FIG. 3, a chemical imaging system 40 according to this aspect of the invention includes an image detector 52, and a point detector 54 of a type different from the image detector. In one embodiment, for example, the image detector is a camera sensitive to visible and ultraviolet radiation emitted by fluorescence, and the point detector is a near-infrared single-point detector. This combination of detectors can be coupled with one or more sources 56 that can be tuned to selected fluorescence excitation frequencies. Other combinations of different types of image and point detectors can also be provided, such as visible image detectors sensitive to the color of a predetermined dye or mid-infrared point detectors.

An advantage of this type of arrangement is that it can obtain chemical image information less expensively than may be possible with other prior art arrangements. Using a relatively inexpensive NIR single-point detector can allow for the detection of chemical information for a whole sample, for example, while the use of an inexpensive visible camera can allow for the detection of the spatial distribution of the chemical components in the sample. Combining the output of these two instruments can provide chemical imaging information that might otherwise only be obtainable using significantly more expensive NIR imaging systems.

In one embodiment, the chemical imaging system 40 uses a synthesis module 44, which is operatively connected to a reference library 42. The synthesis module is operatively connected to outputs of the image detector 52 and the point detector 54 and may also have control outputs operatively connected to inputs of the one or more sources 56. The one or more sources are positioned to illuminate the sample 60 to be imaged, as well as one or more optional reference samples 62. The image detector and point detector are positioned to receive radiation back from the sample(s) and/or reference sample(s). The instrument can be arranged to receive reflectance or transmission measurements.

The synthesis module 44 can access the library 42 to determine how the spatial information from the image detector should be interpreted. This library can include entries for a series of known ingredients, for example, which will allow the instrument to detect how these ingredients are distributed throughout the sample. The use of a library can allow a relatively insensitive image detector to provide spectral-spatial information that it might not otherwise be able to resolve. And if the synthesis and control module is equipped with a series sources having different excitation wavelengths, further spectral-spatial information may be obtained.

In one embodiment, the point detector 54 is kept at a fixed location and optics are provided to enable it to receive radiation from a whole sample area or pharmaceutical tablet. The point detector can also be arranged such that it views a smaller part of the sample. It may even be made to be moveable, such that it can sample or scan regions of interest that may become apparent from the use of the image detector 52.

Figure 4:
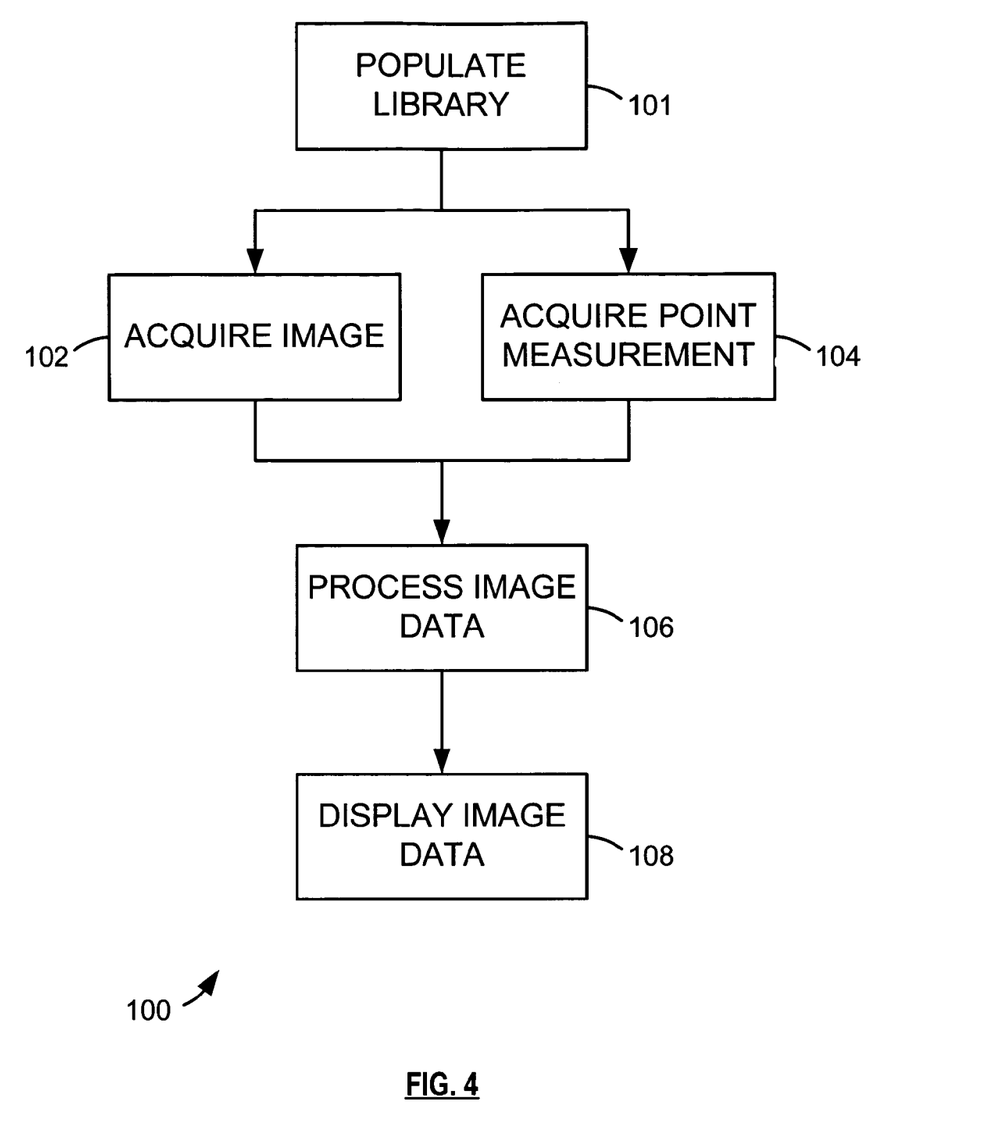
FIG. 4 is a flowchart illustrating the operation of the system of FIG. 3.

Referring also to FIG. 4, operation of the system 40 can begin with the population of the library 42 (step 101). Although other techniques could also be used, this population can be performed using an NIR imaging instrument such as the "Sapphire" instrument available from Spectral Dimensions, Inc. An image and a point measurement can then be acquired, either simultaneously or one before the other (steps 102 and 104). The synthesis module can process the resulting data (step 106). The result can then be conveyed to the user, such as by displaying a chemical image of the sample or by providing a go/no-go indication (step 108).

In one embodiment, the system is based on the so-called IBM-PC architecture, with the synthesis module 44 and user interface 46 being implemented in software. Of course, other structures can be used to implement systems according to the invention, including various combinations of dedicated hardware and special-purpose software running on general-purpose hardware. In addition, the various elements and steps described can be reorganized, divided, and combined in different ways without departing from the scope and spirit of the invention. It should also be noted that not all of the items presented in the discussion of the illustrative embodiment will be required for all implementations of the invention.

Figure 5:
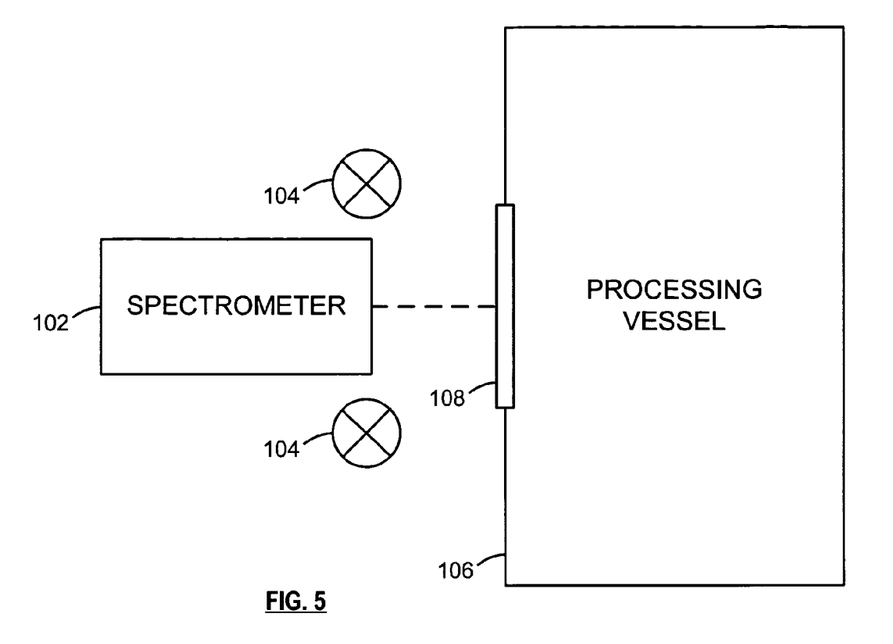
FIG. 5 is a block diagram of an illustrative embodiment of a system used to monitor pharmaceutical mixing.
Figure 6:
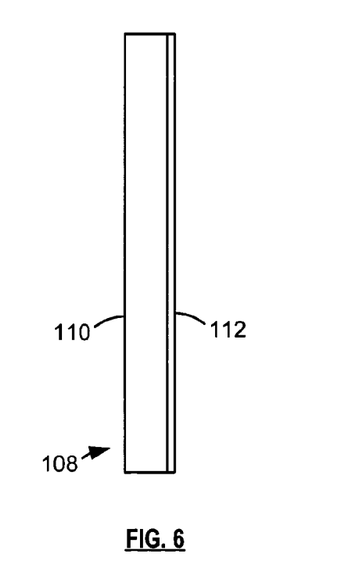
FIG. 6 is a cross-section of a window for the system of FIG. 5.

Referring to FIGS. 5 and 6, it is often desirable to use a spectrometer 102 to monitor the homogeneity of bulk pharmaceuticals while they are held in a processing vessel 106, such as a mixing vessel, conduit, or storage container. In these situations, the vessel is usually outfitted with a window that is transparent to the wavelength used to monitor homogeneity. In the case of an NIR spectrometer, for example, the window can be made out of sapphire, which is highly transparent to infrared radiation.

Unfortunately, the results of such experiments are not always satisfactory, because some of the ingredients used in pharmaceutical mixtures, such as magnesium stearate, may adhere to the vessel's window. This effect may be enhanced when the spectrometer is used in connection with one or more high intensity sources 104. A simple "non-stick" material window 108 can prevent this problem. This type of window includes a material that is transparent in the spectral region of interest, but it does not adhere to the pharmaceutical mixture.

The window 108 can be made entirely of the non-stick material, or it can be part of a compound structure in which a non-stick material is associated with another material. For ultraviolet or infrared imaging, for example, a window made of a structural sapphire portion 110 adjacent a polytetraflouoroethylene non-stick portion 112 can be used. The sapphire in this compound window gives it strength, while the polytetraflouoroethylene prevents degradation of results due to adherence of material on the window. Both materials exhibit very good UV and NIR transparency.

The non-stick portion can be made of a number of different materials that resist adherence by pharmaceutical ingredients. For example, fluoropolymers such as polytetraflouoroethylene can be used. These fluoropolymers can be used in any appropriate form, such as in the form of a coating or film. Flouropolymers are available, for example, from DuPont (e.g., Teflon). The material in the structural portion of the window can be sapphire, low-OH quartz, CaF2, or other optical grade materials that transmit in the wavelength region of interest. These materials are available from a number of sources, such as the Newport Corporation of Irvine Calif.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

What is claimed is:

1. An apparatus for obtaining information about a heterogeneous pharmaceutical mixture, comprising:
a visible-range image acquisition system having a field of view operative to acquire images of samples of the pharmaceutical mixture, wherein the pharmaceutical mixture includes a plurality of components each having different chemical properties,
an image enhancement detection module optimized to detect portions of the mixture corresponding to the different components having been affected differently by exposure to a predetermined image enhancement agent, and
an information derivation module responsive to the image enhancement detection module and operative to derive information about a distribution of the components of the mixture in the image, based on spatial information derived from the different effects of the exposure detected by the image enhancement detection module.

2. A chemical imaging system for pharmaceutical analysis, comprising:
a spectrometric imaging detector having a first sensitivity range that includes at least a portion of the visible range between a first wavelength and a second wavelength longer than the first wavelength, wherein the spectrometric imaging detector is operative to acquire an image of a pharmaceutical mixture in a sample area,
a spectrometric point detector having a second sensitivity range between a third wavelength and a fourth wavelength longer than the third wavelength, wherein the first and second wavelengths ranges are different, wherein the spectrometric point detector is operative to acquire a reading of the pharmaceutical mixture in the sample area, and
a synthesis module responsive to the imaging detector and to the point detector and being operative to operate on output from the imaging detector and output from the point detector to obtain a quality metric for the pharmaceutical mixture.

3. The apparatus of claim 2 wherein the quality metric includes a chemical image of the pharmaceutical mixture.

4. The apparatus of claim 2 wherein the pharmaceutical mixture is in the form of a pharmaceutical tablet.

5. The apparatus of claim 2 further including threshold detection logic operative to determine whether the quality metric meets a predetermined quality standard.

6. The apparatus of claim 2 further including threshold detection logic operative to determine whether the quality metric meets a predetermined origin standard.

7. The apparatus of claim 6 further including threshold detection logic operative to determine whether the quality metric meets a predetermined authenticity standard.

8. The apparatus of claim 2 further including statistical analysis logic operative to derive statistical information about the spatial distribution of components of the mixture.

9. The apparatus of claim 8 wherein the statistical analysis logic is operative to derive information about particle size for components of the mixture.

10. The apparatus of claim 8 wherein the statistical analysis logic is operative to derive information about particle distribution for components of the mixture.

11. The apparatus of claim 2 further including a radiation source positioned to illuminate the sample.

12. The apparatus of claim 11 wherein the radiation source is an ultraviolet light emitting diode.

13. The apparatus of claim 11 wherein the radiation source is a visible light emitting diode.

14. The apparatus of claim 2 further including a plurality of radiation sources positioned to illuminate the sample.

15. The apparatus of claim 2 wherein the spectrometric point detector is a Raman point detector.

16. The apparatus of claim 2 wherein the spectrometric point detector is an infrared point detector.

17. The apparatus of claim 2 wherein the spectrometric point detector is a near infrared point detector.

18. The apparatus of claim 2 further including at least one spectrally selective element between a radiation source and the imaging detector.

19. The apparatus of claim 2 wherein the chemical imaging system is operative to acquire an image of a reference with the image of the pharmaceutical mixture.

20. The apparatus of claim 1 wherein the information derivation module includes statistical analysis logic.

21. The apparatus of claim 20 wherein the statistical analysis logic is operative to determine information about particle size.

22. The apparatus of claim 20 wherein the statistical analysis logic is operative to determine information about particle distribution.

23. The apparatus of claim 20 wherein the statistical analysis logic is operative to determine information from a plurality of acquisitions.

24. The apparatus of claim 20 wherein the statistical analysis logic is operative to derive information about a range of variation of properties of one or more components of the sample.

25. The apparatus of claim 1 wherein the information derivation module is operative to compare information about distributions of components of different samples of the pharmaceutical mixture.

26. The apparatus of claim 1 wherein the information derivation module is operative to compare information about a distribution of components of a sample with a predetermined reference standard.

27. The apparatus of claim 1 wherein the information derivation module is operative to provide an indication of origin.

28. The apparatus of claim 27 wherein the information derivation module is operative to provide a genuine/counterfeit indication.

29. The apparatus of claim 27 wherein the information derivation module is operative to provide a cleaning validation.

30. The apparatus of claim 27 wherein the information derivation module is operative to provide an indication of a root cause of a process defect.

31. The apparatus of claim 1 further including a visible light source positioned to illuminate at least part of the field of view of the visible-range image acquisition system.

* * * * *